United States Patent [19]

Young

[11] Patent Number: 5,006,801
[45] Date of Patent: Apr. 9, 1991

[54] EDDY CURRENT INSPECTION PROBE WITH PROBE COIL RESONACE REDUCTION

[75] Inventor: John D. Young, Rexford, N.Y.

[73] Assignee: General Electric Company, Schenectady, N.Y.

[21] Appl. No.: 360,687

[22] Filed: Jun. 2, 1989

[51] Int. Cl.[5] ............... G01N 27/82; G01N 27/72; G01R 33/00; G01R 33/12
[52] U.S. Cl. ................... 324/238; 324/225
[58] Field of Search ........... 324/238, 240, 241, 242, 324/243, 225, DIG. 1, 158 P, 72.5

[56] References Cited

U.S. PATENT DOCUMENTS

| | | | |
|---|---|---|---|
| 3,050,678 | 8/1962 | Datt | 324/238 |
| 3,056,081 | 9/1962 | Hochschild | 324/37 |
| 3,444,465 | 5/1969 | Teixeira | 324/72.5 |
| 3,487,298 | 12/1969 | Gill et al. | 324/238 |
| 3,732,726 | 5/1973 | Ferber | 73/67.5 R |
| 3,825,822 | 7/1974 | Forster | 324/40 |
| 3,886,793 | 6/1975 | Cramer et al. | 73/167 |
| 4,074,186 | 2/1978 | Flaherty | 324/222 |
| 4,088,953 | 5/1978 | Sarian | 324/232 |
| 4,109,201 | 8/1978 | Pigeon et al. | 324/227 |
| 4,167,878 | 9/1979 | Bottcher et al. | 73/601 |
| 4,176,555 | 12/1979 | Doorman | 324/611 |
| 4,335,352 | 6/1982 | Stephen | 324/228 |
| 4,412,177 | 10/1983 | Petrini et al. | 324/226 |
| 4,414,508 | 11/1983 | Davis et al. | 324/238 |
| 4,449,411 | 5/1984 | Suhr et al. | 73/643 |
| 4,460,869 | 7/1984 | Buser et al. | 324/200 |
| 4,528,856 | 7/1985 | Junker et al. | 73/779 |
| 4,564,810 | 1/1986 | Geithman et al. | 324/230 |
| 4,591,784 | 5/1986 | Kolitsch et al. | 324/208 |
| 4,659,990 | 4/1987 | Torre | 324/238 |
| 4,673,877 | 6/1987 | Sakamoto et al. | 324/225 |
| 4,745,809 | 5/1988 | Collins et al. | 73/661 |
| 4,808,926 | 2/1989 | Graham et al. | 324/226 |
| 4,856,337 | 8/1989 | Metala et al. | 73/601 |
| 4,862,079 | 8/1989 | Chickering et al. | 324/227 |

OTHER PUBLICATIONS

Hedengren, McCary, Young, "Eddy Current Probe Evaluation: Experimental Measurements and System Interaction", Review of Progress in Quantitative Nondestructive Evaluation, vol. 8A, Plenum Publishing Corporation, 12/1989, pp. 975–983.

Standard Handbook for Electrical Engineers, Eleventh Edition, McGraw-Hill Book Company, 12/1978, pp. 3-48–3-57.

Primary Examiner—Walter E. Snow
Attorney, Agent, or Firm—John S. Beulick; James C. Davis, Jr.; Paul R. Webb, II

[57] ABSTRACT

The present invention is an inspection instrument of the type which reacts to induced eddy currents in a workpiece to be inspected and includes a probe having at least a first probe coil. The instrument further includes a bridge circuit having the first probe coil connected in a first bridge arm. The bridge circuit also has input and output terminals. Connecting cable connects the instrument to a remote signal interpretation unit, and individual buffers connected between each of the output terminals and the cable isolate the capacitive of the cable from the bridge circuit.

9 Claims, 2 Drawing Sheets

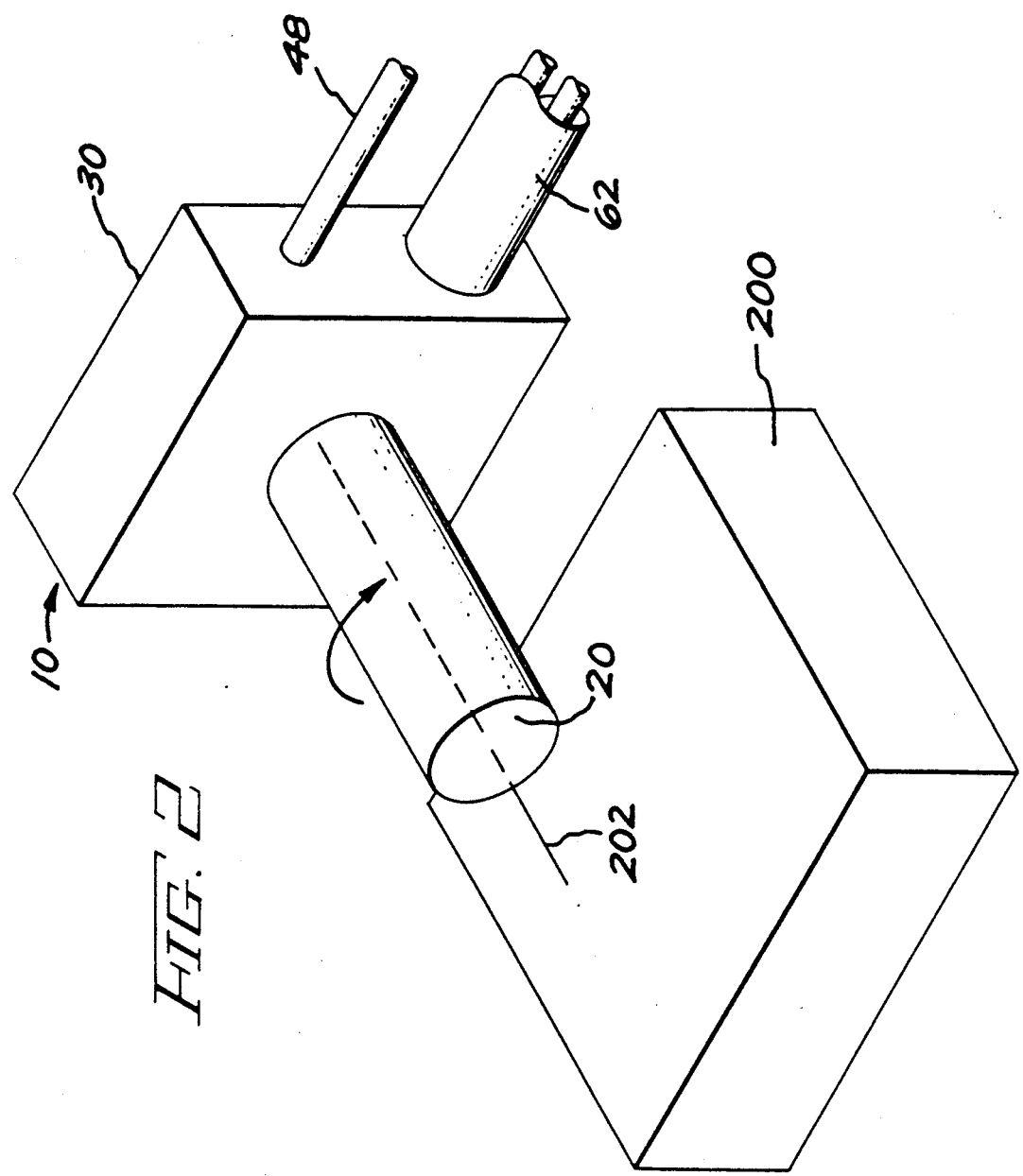

EDDY CURRENT INSPECTION PROBE WITH PROBE COIL RESONACE REDUCTION

The present invention relates in general to an inspection instrument for measuring discontinuities in a workpiece and more specifically to an inspection instrument of the type which reacts to induced eddy currents in a workpiece to be inspected.

BACKGROUND OF THE INVENTION

Inspection instruments of the type under discussion here are capable of detecting cracks and other deformations is a workpiece by measuring the eddy current induced in the workpiece. The term eddy current, as generally understood in the art and as used herein, refers to a current created or induced in a conductor by an applied varying magnetic field, or by moving the conductor in a magnetic field.

Known instruments that utilize the eddy current effect generally include a probe having one or more probe coils intended to be positioned adjacent the workpiece. Although different probes will have different dimensions, by way of example, a probe may be about one-tenth of an inch in diameter and about three inches in length.

One type of probe, known in the art as a split core differential probe, has a pair of probe coils symmetrically spaced from a central axis. The probe is rotatably engaged to a small motor or the like for rotating the probe with respect to the axis. The probe coil leads extend through the motor, by way of slip rings or the like, and are connected to a cable which at its other end is connected to other circuit elements and to a signal interpretation unit. The probe coils form part of a measuring circuit, such as a bridge circuit, together with the aforesaid circuit elements.

Before a workpiece can be inspected, the instrument must be calibrated. With both probe coils positioned remote form any conductor, the motor rotates the probe and an AC drive signals is applied to the bridge circuit at a selected frequency. The output signal of the bridge circuit in this condition serves as the calibration signal.

The magnitude of the calibration signal can be adjusted by varying the impedance of the bridge arms, for example by substituting different circuit components. Since two of the bridge arms generally include a reactive impedance which varies with the frequency of the drive signal, the frequency of the applied drive signal must remain constant during calibration and inspection.

To inspect a workpiece, the probe is brought adjacent the latter and the probe coils are rotated at a constant rate. Thus, each probe coil will move proximate the workpiece and then away from it during one complete rotation. The magnetic field produced by each probe coil due to the combined effect of the applied AC drive signal and the coil movement induces an eddy current in the workpiece.

The magnetic field created by the eddy current interacts with the magnetic field of whichever probe coil is proximate the workpiece at a given instant. This interaction causes a change in the impedance of the proximate probe coil while the impedance of the other probe coil of the pair, i.e., the one remote from the workpiece, remains substantially at its calibration value. The bridge circuit therefore becomes unbalanced and the resultant output signal is representative of the magnitude of the eddy current. When the previously more remote probe coil moves to a position proximate the workpiece, the situation is reversed and the bridge circuit again becomes unbalanced. Thus, the bridge circuit becomes unbalanced twice in each rotation of the probe.

As the rotating probe is passed along the workpiece, cracks and other discontinuities of deformations in the workpiece will produce changes in the magnitude of the induced eddy current as compared to the magnitude of the induced eddy current in areas that do not have these anomalies. This results in corresponding variations in the magnitude of the impedance changes which the probe coils undergo during rotation and the impedance changes thus affect the bridge circuit output signal. Hence, the output signal, specifically the amplitude of the output signal variations, is a measure of the condition of the workpiece.

In the above-described instrument, the probe and the motor must be portable and they may have to operate at a considerable distance from the remaining bridge circuit elements mentioned above. The connecting cable therefore is of appreciable length and its capacitive reactance must be taken into account in adjusting, calibrating and operating the bridge circuit at the frequency of the applied AC signal.

Specifically, at the frequency of the drive signal, the capacitive reactance of the cable may resonate with the inductive reactance of the coils. If resonance does occur, the generated noise will deteriorate the signal-to-noise ratio of the bridge circuit output signal. Under these conditions, the point at which resonance occurs will be below the self-resonance frequency of the probe coils and it will thereby limit the operating frequency range of the bridge circuit.

Heretofore, the problems discussed above, particularly the problem of generated noise, were often attributed to poor coil construction and/or design and the suspect probes were discarded. That practice materially increased the cost of making the measurements without a commensurate increase in accuracy. Further, in practice it is not uncommon to use different lengths of cable as required by the particular workpiece. For example, when using existing instruments to inspect bolt holes in an aircraft engine, the signal interpretation unit generally is kept stationary and an operator walks around the engine with the rotating probe to inspect each bolt hole. Since it is preferable to use as short a cable as possible in order to reduce the reactance introduced by the cable, a shorter cable may be substituted for bolt holes located close to the instrument.

Since the connecting cable connects the probe coils to the remaining bridge circuit elements in the instruments described, the cable reactance becomes part of the bridge circuit impedance. Hence, the impedance of the bridge circuit components must be re-adjusted whenever cables of different length, and hence of different capacitive reactance, are exchanged in order to maintain a calibration signal of constant amplitude. Such a re-adjustment procedure can be time consuming and it presents serious constraints on the utility of present day inspection instruments in a busy work environment.

OBJECTS OF THE INVENTION

It is therefore an object of the present invention to provide a new and improved inspection instrument of the type which reacts to induced eddy currents, which overcomes the foregoing disadvantages and shortcomings of known instruments.

Another object of the present invention is to provide a new and improved inspection instrument wherein the possibility of unwanted circuit resonance is substantially reduced.

Yet another object of the present invention is to provide an inspection instrument which facilitates a quick and accurate determination of flaws in a workpiece.

Still another object of the present invention is to provide an inspection instrument wherein there is no need to re-adjust the bridge circuit whenever a cable of a different length is used.

Another object of the present invention is to provide a movable inspection instrument wherein the probe and the bridge circuit are formed as a movable unit, and the movable unit is connected by a buffer-isolated cable to a stationary signal interpretation unit.

Yet another object of the present invention is to provide an inspection instrument wherein the inductance characteristics of different probes can be accurately matched by the use of appropriate matching capacitors without having to take into consideration the impedance of the connecting cable.

SUMMARY OF THE INVENTION

In accordance with the present invention, the novel inspection instrument is a movable unit which includes a rotatable probe having at least one probe coil connected in a first bridge arm of an AC drive bridge circuit. A connecting cable connects the bridge circuit output terminals to a remote stationary signal interpretation unit. Individual buffers are connected between each output terminal and the connecting cable to isolate the capacitive reactance of the cable from the bridge circuit and to prevent undesired resonance conditions at the frequency the AC drive signal.

The connection between the probe coils and the other bridge elements is short and its capacitive impedance is negligible at the frequency of the AC drive signal. Further, with the reactance of the connecting cable isolated by the buffers, the accuracy of the measurements taken is materially enhanced and the possibility that the probe coils and cable will become resonant at the operating frequency is substantially eliminated.

The present invention permits the bridge circuit to operate reliably at frequencies up to the self-resonance frequency of the probe coils, thus expanding the operating range of the present instrument over the operating range of known devices. Also, for a chosen operating frequency, matching capacitors may be selected to adjust the ratio of impedances between the bridge circuit arms for different probes, and the bridge circuit does not need re-adjusting each time a different length cable is used.

These features substantially reduce problems associated with the use of different probes and/or cables of different lengths and meaningful comparisons between probes of different vendors are therefore possible. The present invention also provides an improved signal-to-nose ratio of the output signal derived from the inspection instrument, thereby further improving the accuracy of the measurements.

BRIEF DESCRIPTION OF THE DRAWINGS

These and other objects of the present invention, together with further features and advantages thereof, will become apparent from the following detailed specification when read together with the accompanying drawings, in which:

FIG. 2 shows the inspection instrument of FIG. 1 in position to inspect a workpiece.

DETAILED DESCRIPTION OF THE PREFERRED EMBODIMENT

Figure 1:
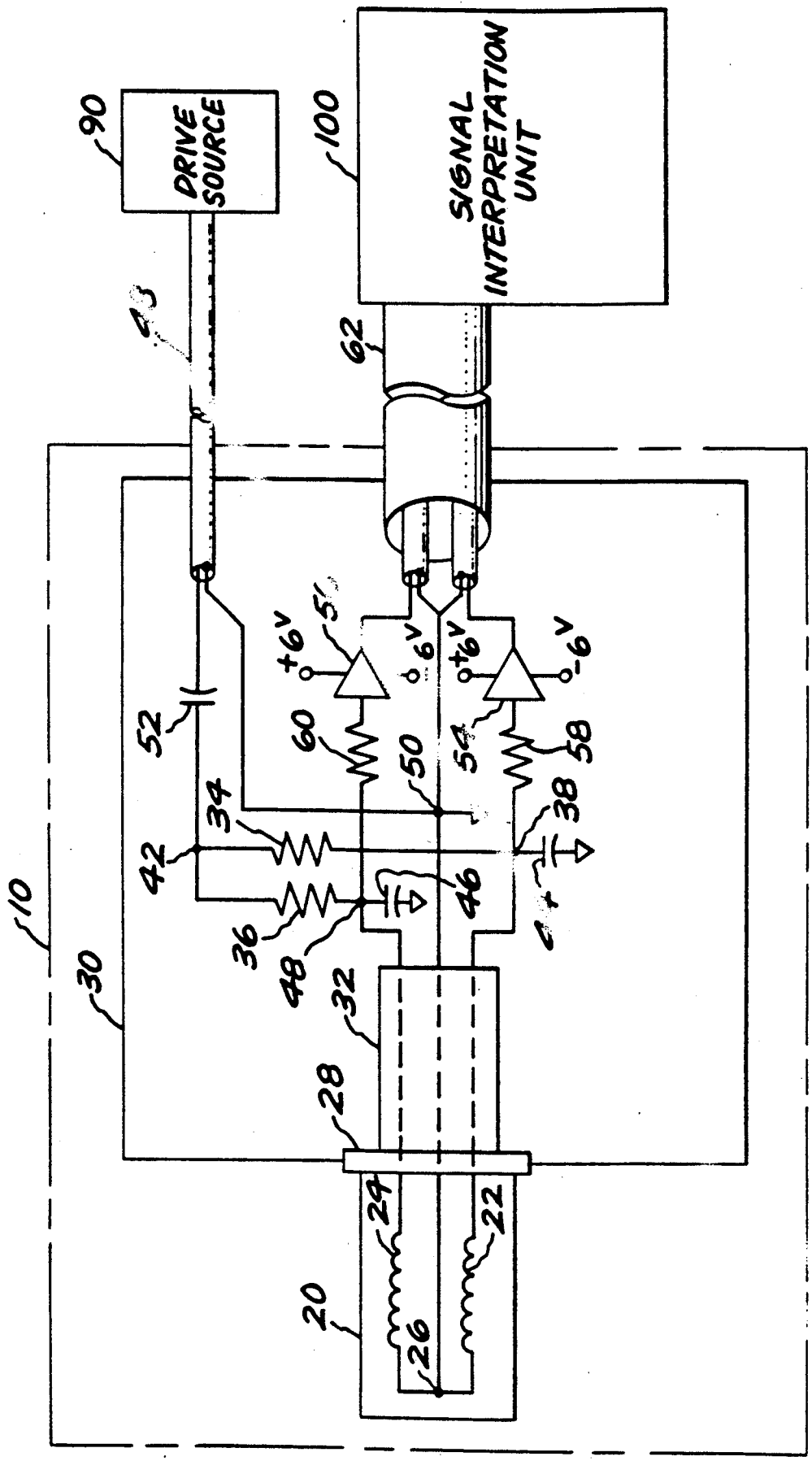
FIG. 1 is a schematic illustration of a preferred embodiment of an inspection instrument in accordance with the present invention.

FIG. 1 illustrates an inspection instrument 10 which includes a probe 20, shown as a split core differential probe, and an instrument portion 30 which contains the remaining circuit elements. The inspection instrument is connected to an AC drive source 90 and to a signal interpretation unit 100. Instrument 10 is not drawn to scale in FIG. 1 and, by way of example, probe 20 generally is about one-tenth of an inch in diameter and drive source 90 and unit 100 are relatively large as compared to instrument 10.

Probe 20 is removably and rotatably mounted to instrument portion 30. The probe includes a pair of probe coils 22 and 24 connected at a first bridge node 26, the latter being grounded. The probe coil leads and the grounded lead extend into the instrument portion via slip rings 28 or like devices, and through a motor 32 which is connected to rotate the probe relative to the instrument portion.

In accordance with the preferred embodiment of the present invention, instrument portion 30 includes a pair of resistors 34 and 36 which are coupled to first and second coils 22 and 24, respectively, at second and third nodes 38 and 40, respectively. Resistors 34 and 36 are connected at fourth node 42. Coils 22 and 24 and resistors 34 and 36 are connected so as to form a measuring circuit, generally referred to herein as a bridge circuit. Coils 22 and 24 preferably have substantially equal inductances and resistors 34 and 36 preferably have substantially equal resistances to facilitate developing desired output signals at nodes 38 and 40, as hereinafter discussed.

The inspection instrument includes a pair of matchings capacitors 44 and 46 coupled between nodes 38 and 40, respectively, and ground. First bridge node 26 is connected to grounded node 50, and an input cable 46 is connected to nodes 42 and 50. Input cable 48 couples drive source 90, such as a 2 Mhz sinusoidal source, to nodes 42 and 50, which serve as input terminals of the bridge circuit. The drive source is AC coupled to the bridge circuit by means of a capacitor 52 which prevents the drive signal generated by the drive source from including any DC offset.

Nodes 38 and 40, which are the output terminals of the bridge circuit, are coupled to a pair of buffer isolation amplifiers 54 and 56, respectively, by way of a pair of resistors 58 and 60, respectively. Resistor 58 and 60 serve to bias buffers 54 and 56 which include a high input impedance. Buffers 54 and 56 are coupled to a connecting cable 62 which is a coaxial cable coupled at its other end as an input to the signal interpretation unit.

Before inspecting a workpiece, appropriate capacitance matching capacitors 44 and 46 must be selected. Second probe coil 24 preferably has the same impedance as first probe coil 22 so that the capacitance for both matching capacitors 44 and 46 can be determined by a single calculation. The required capacitance of matching capacitors 44 and 46 can be determined from the following equation:

$$C = [1/(w^2L)][1-(jwL)/(j200)] \qquad (1)$$

where
- j200 = impedance (ohms) of the respective bridge arm,
- w = operating angular frequency (radians per second),
- L = inductance (henrys) of coils 22 and 24, and
- C = capacitance (farads) of matching capacitors 44 and 46.

A reactance for each bridge arm which has a probe coil connected therein of approximately 200 ohms provides a preferred signal-to-noise ratio, and matching these bridge arm impedances with this magnitude of reactance increases the sensitivity of the probe coils. The inductance of first and second coils 22 and 24 can simply be measured, and the operating angular frequency can easily be calculated from a selected operating frequency. Thus, the capacitance of capacitors 44 and 46 can be calculated. Further, before operation and rather than being biased at normal voltage such as fifteen volts, buffers 54 and 56 may be biased at reduced voltages, such as six volts, in order to reduce thermal drift therein.

In operation, but before inspecting a workpiece, drive source 90 is activated and the drive signal is transmitted to the bridge circuit. As the probe is rotated in air, a signal representative of this condition is transmitted from nodes 38 and 40 to the signal interpretation unit 100 by way of resistors 58, 60, buffers 54, 56 and cable 62. The signal received by the interpretation unit under this condition is the calibration signal, and the reading of the interpretation unit may be adjusted accordingly.

Preferably, in this condition, the previous adjustment of the matching capacitors, as hereinbefore described, provides that the voltage at node 38 equals the voltage at node 40. Capacitors 44 and 46 are selected so that probe coils having different inductance values will provide an identical calibration signal at a fixed operating frequency. More specifically, the ratio of the voltage at node 38 to the voltage at node 40 can be adjusted via matching capacitors 44 and 46 so that the same ratio exists regardless of the inductance of the probe coils.

Referring to FIG. 2, when inspecting an electrically conductive workpiece 200 with instrument 10 previously calibrated as hereinbefore described, as probe 20 rotates relative to instrument portion 30, the probe is placed adjacent the workpiece. Axis 202, shown partially hidden, is the axis about which the probe coils rotate. A magnetic field is created by the combination of the rotation of the probe coils and alternating current passing through the coils. The magnetic field of each probe coil, as it is brought adjacent the workpiece, induces an eddy current in the workpiece. The eddy current, in turn, produces a magnetic field which interacts with the magnetic field of the adjacent probe coil and causes a change of impedance of the latter. The impedance of the other, more remote probe coil at this tims is substantially unchanged.

As the probe coils rotate and are alternately brought adjacent the workpiece, the coil more remote from the workpiece has an impedance substantially equal to its initial calibration value while the impedance of the coil adjacent the workpiece changes in accordance with the magnitude of the induced eddy current. In this manner, the rotating probe coils alternately cause the bridge circuit to become unbalanced and this unbalanced condition results in a different voltage ratio between the signals present at nodes 38 and 40. The output signal received at the signal interpretation unit is thus representative of the induced eddy current.

If the probe is maintained at a same distance from the workpiece as it is moved along the latter, the magnitude of the eddy current induced by the probe coils will remain substantially the same. Any crack or other deformation in the workpiece, however, presents a discontinuity of the path of the eddy current and will therefore affect the magnetic flux created by the eddy current. As such, a deformation will cause variations of the impedance changes probe coils 22 and 24 undergo, and hence the signals appearing at nodes 38, 40 are indicative of the condition of the workpiece.

Buffer isolation amplifiers 54 and 56 present a high impedance between connecting cable 62 and the probe coils. This isolation of the capacitive impedance of the cable from the coils materially reduces the possibility that the coils and cable will become resonant at the frequency of the drive signal. It also permits the instrument to operate at frequencies up to the self-resonance frequency of the probe coils with the previously mentioned capacitors removed. Buffers 54 and 56 also substantially isolate any noise generated by the coils-cable resonance from the signal interpretation unit. Thus, the signal-to-noise ratio of the output signal transmitted to the interpretation unit is improved significantly resulting in improved operation and greater accuracy of the instrument.

Further, before now it was difficult and tedious to calculate a value for matching capacitors because the impedance, including capacitance reactance, of a connecting cable was part of the bridge circuit, and as explained above, whenever a cable of different length was used, the bridge circuit of heretofore available instruments had to be re-adjusted. In the present invention, the impedance of the connecting cable is isolated from the bridge circuit thus making it easier to determine the appropriate capacitance for the matchine capacitors. Also, with the present invention, different length cables can be used with the same instrument without affecting the output signal from the bridge circuit. These features provide that testing and comparison of various probes in actual operating conditions are possible, and any probe sensitivity differences can be related to each respective probe construction rather than to other considerations such as the length of the connecting cable.

While the present invention has been described with respect to a specific embodiment, many modifications, variations, substitutions, and equivalents will now be apparent to those skilled in the art. For example, variable resistors and capacitors could be connected in each bridge arm to further facilitate generating a desired voltage ratio between the signals present at nodes 38 and 40 of the present invention.

Also, various types of probes such as an absolute probe having a pair of coils, one of the coils being isolated and prevented from being affected by the eddy current induced in the workpiece, may be utilized. With an absolute probe, only one coil is rotated and brought adjacent the workpiece. Accordingly, the invention is to be considered as limited only by the spirit and scope of the appended claims.

What is claimed is:

1. An inspection instrument of the type which reacts to induced eddy currents in a workpiece to be inspected, said instrument comprising:
   a probe including a first probe coil and a second probe coil;
   a bridge circuit including said first probe coil connected in a first bridge arm, said second probe coil connected in a second bridge arm, a first and a second resistor connected in third and fourth bridge arms respectively, said first and second bridge arms connected at a grounded first bridge node, said first and third bridge arms connected at a second bridge node, said second and fourth bridge arms connected at a third bridge node, said third and fourth bridge arms connected at a fourth bridge node, said first and fourth bridge nodes constituting input terminals for receiving an AC drive signal, and said second and third bridge nodes constituting output terminals;
   first and second capacitors coupled between said second and third bridge nodes respectively and ground;
   means for connecting said bridge output terminals to a remote signal interpretation unit, said connecting means having a capacitive reactance value capable of producing undesired resonance conditions with said probe coil at the frequency of said AC drive signal; and
   individual buffer means connected between each of said output terminals and said connecting means to isolate said capacitance reactance from said bridge circuit.

2. An inspection instrument in accordance with claim 1 wherein the capacitance of each of said first and second capacitors is:

$$C = [1/(w^2 L)][1 - (jwL)/(j200)];$$

where
   w = operating angular frequency,
   L = inductance of each of said first and second probe coils, and
   j200 = impedance of each of said first and second bridge arms.

3. An inspection instrument in accordance with claim 1 wherein said first and second probe coils are selected to provide substantially equal impedance values of said first and second bridge arms, and said first and second resistors are selected to provide substantially equal impedance values of said third and fourth bridge arms.

4. An inspection instrument in accordance with claim 1 wherein said AC drive signal is coupled to said input terminals by way of a capacitor.

5. An inspection instrument in accordance with claim 1 where the impedance of each of said first and second bridge arms is selected to be about 200 ohms at a 2 Mhz operating frequency of said AC drive signal.

6. An inspection instrument in accordance with claim 1 where said instrument is movable relative to said workpiece;
   said probe constituting a separate unit of said instrument; and
   means for rotating said probe relative to the remaining portion of said instrument.

7. An inspection instrument in accordance with claim 6 wherein said probe is rotatable about its own axis;
   said first and second probe coils spaced from and parallel to said axis;
   whereby the rotation of said probe alternately brings said first and second probe coils into proximity with the inspected workpiece portion when said instrument is placed adjacent said workpiece.

8. An inspection instrument in accordance with claim 6 wherein said probe is rotatable about its own axis;
   said first probe coil spaced from and parallel to said axis;
   whereby the rotation of said probe brings said first probe coil into proximity with the inspected workpiece portions when said instrument is placed adjacent said workpiece.

9. An inspection instrument in accordance with claim 1 wherein each of said individual buffer means comprises a resistance connected in series with an operational amplifier.

* * * * *